Figure 1:
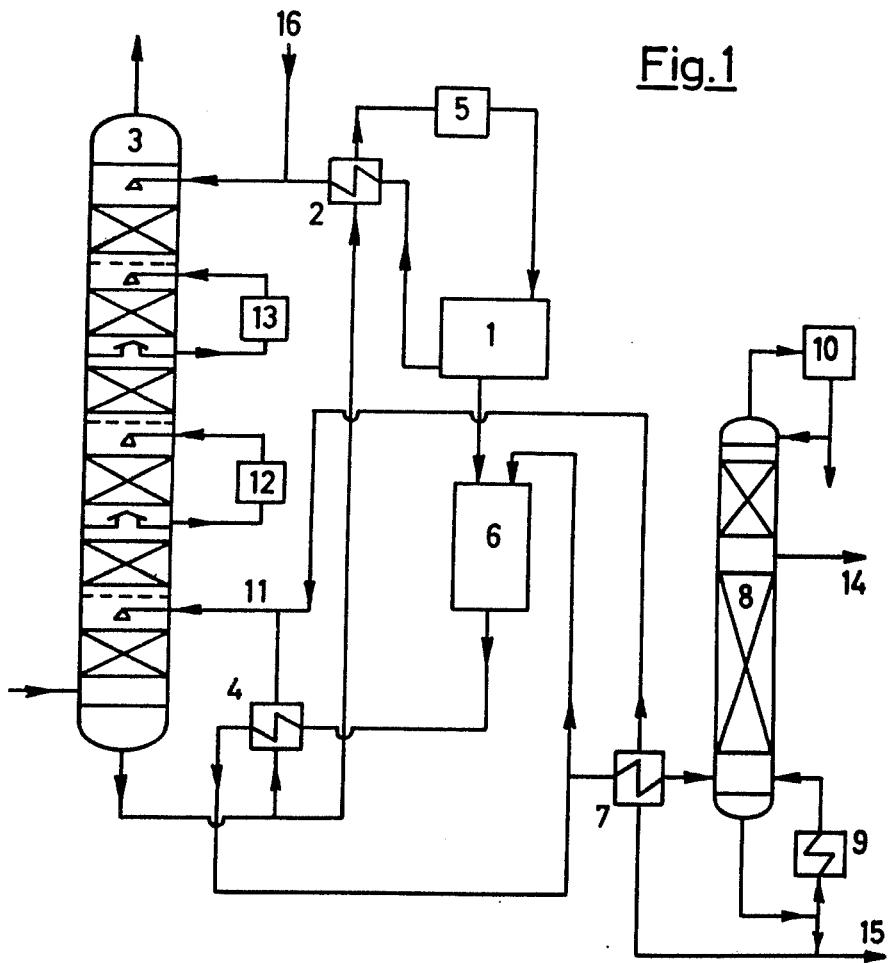

United States Patent [19]
Wirth et al.

[11] 4,008,255
[45] Feb. 15, 1977

[54] RECOVERY OF PHTHALIC ANHYDRIDE

[75] Inventors: Friedrich Wirth; Wolfgang Kube; Paul Hornberger; Otto Leman; Joachim Wagner, all of Ludwigshafen; Dieter Karau, Oftersheim, all of Germany

[73] Assignee: BASF Aktiengesellschaft, Ludwigshafen (Rhine), Germany

[22] Filed: June 23, 1975

[21] Appl. No.: 589,566

Related U.S. Application Data

[63] Continuation of Ser. No. 451,135, March 14, 1974, abandoned.

[30] Foreign Application Priority Data

Mar. 17, 1973 Germany .......................... 2313306

[52] U.S. Cl. ............................ 260/346.4; 203/42; 203/48; 203/52; 203/70; 260/346.7
[51] Int. Cl.² ........................................ C07D 307/89
[58] Field of Search ................. 203/42, 48, 70, 52, 203/68, 69; 260/346.7, 346.4

[56] References Cited

UNITED STATES PATENTS

| | | | |
|---|---|---|---|
| 2,893,924 | 7/1959 | Courtier | 203/70 |
| 2,942,005 | 6/1960 | Brown | 260/346.7 |
| 3,040,060 | 6/1962 | Kulik | 260/346.7 |
| 3,187,016 | 6/1965 | Brown et al. | 260/346.4 |
| 3,462,461 | 8/1969 | Bloom | 260/346.7 |

Primary Examiner—Wilbur L. Bascomb, Jr.
Attorney, Agent, or Firm—Johnston, Keil, Thompson & Shurtleff

[57] ABSTRACT

Process for the recovery of phthalic anhydride in which gases as obtained in the catalytic atmospheric oxidation of o-xylene or naphthalene are treated with a hydrocarbon containing $C_{26-44}$ paraffins, cooling, if necessary, the hydrocarbon laden with phthalic anhydride, separating the solid phthalic anhydride followed by melting and distillation thereof.

6 Claims, 2 Drawing Figures

RECOVERY OF PHTHALIC ANHYDRIDE

This is a continuation, of application Ser. No. 451,135 filed Mar. 14, 1974, which application has now been abandoned.

This application discloses and claims subject matter described in German patent application P 23 13 306.4, filed Mar. 17, 1973, which is incorporated herein by reference.

This invention relates to the continuous recovery of phthalic anhydride from process gases obtained by catalytic atmospheric oxidation of o-xylene or naphthalene.

Large-scale manufacture of phthalic anhydride is effected by catalytic atmospheric oxidation of o-xylene or naphthalene. This oxidation is carried out in a fixed-bed or fluidized bed reactor. To avoid explosions, this oxidation is carried out with a large excess of air, with the result that the product must be separated from a gas in which the partial pressure of the product is very low. Thus separation is costly, and the isolation of phthalic anhydride from these process gases is consequently a significant process step both technologically and economically.

The most common method of recovering phthalic anhydride from process gases is to desublimate the product on heat-exchanging surfaces. This is effected by using large cooled chambers which are accessible from the outside and which must be periodically emptied mechanically. It is preferred to use finned-tube condensers, in which the tubes are cooled to cause the phthalic anhydride to desublimate on the fins thereof, which are then periodically heated to cause melting of the phthalic anhydride. This method requires a number of such condensers used in parallel. This isolation of the crude product is followed by a purifying stage, in which the phthalic anhydride is freed from by-products.

The separation of phthalic anhydride involves very great expense in terms of capital expenditure, space requirements and maintenance costs. Since the purification of the crude product may be carried out continuously by fractional distillation in all large plants, the batchwise operation of the separating unit constitutes a disadvantage. In such units, steel equipment having a large thermal capacity must be periodically heated and cooled. The energy consumption in such a procedure is greater than in continuous operations. Furthermore, the constant temperature changes during operation of the equipment increase the stresses on the material thereof, which calls for sturdier and thus more expensive equipment.

For this reason, attempts have been made to simplify the recovery of phthalic anhydride by treating the process gases with solvents. In a process described in French Pat. No. 1,121,645, the process gases are washed with pentadecane or tetradecane. The phthalic anhydride is then isolated from the resulting solutions by azeotropic distillation. This method cannot produce commercial-grade phthalic anhydride having heat-color numbers (Hazen) of less than 60.

We have now found that phthalic anhydride may be continuously recovered, in a particularly advantageous manner, by treating process gases such as are obtained in the catalytic atmospheric oxidation of o-xylene or naphthalene with a hydrocarbon as solvent and separating the phthalic anhydride from the hydrocarbon by distillation, provided that the process gases are treated with a hydrocarbon containing $C_{26-44}$ paraffins at temperatures not below 60° C and that the hydrocarbon laden with phthalic anhydride is cooled, if necessary, to less than 135° C, the solid phthalic anhydride then being separated from the solvent in the form of a slurry, whilst the solution is recycled to the process gas treatment stage, the phthalic anhydride being distilled from the slurry after melting.

Our novel process starts from process gases obtained in the well-known catalytic atmospheric oxidation of o-xylene or naphthalene. These gases, which contain approximately 35 to 45 g of phthalic anhydride per $m^3$ (STP) and have a temperature of, say, 140°–170° C, are advantageously passed upwardly through a column (hereinafter referred to as the wash column), in which they are treated with a countercurrent of paraffinic hydrocarbons at a temperature of not less than 60° C and advantageously at atmospheric pressure.

The hydrocarbons to be used as solvents in the process of the invention are $C_{26-44}$ paraffins and preferably $C_{26-38}$ paraffins or mixtures containing at least 55% and preferably at least 60% by weight of said paraffins and also containing, if desired, naphthenes or aromatic compounds, the aromatic portion being not more than 10% and preferably not more than 5% by weight of the mixture. The boiling point of the hydrocarbon or hydrocarbon mixture is above 360° C.

The solent leaves the wash column at a temperature of, say, 70°–140° C and preferably 90°–135° C, being laden with from 0.5 to 40% by weight of phthalic anhydride. The solvent laden with phthalic anhydride is, if necessary, cooled to temperatures below 135° C, advantageoulsy to 60°–40° C, during which process the major portion of the phthalic anhydride separates in solid form. The phthalic anhydride crystals are then separated from the major portion of the solvent by mechanical means, for example with a centrifuge or filter, to give a slurry of the crystals in solvent. This slurry contains from about 30 to 70% by weight of phthalic anhydride. The solvent separated from the solid phthalic anhydride and having a phthalic anhydride content of from 0.3 to 3% by weight, is returned to the wash column. The slurry is heated to temperatures of from 130° to 150° C to melt the phthalic anhydride crystals and is then treated by distillation to remove the phthalic anhydride from the solvent residues and from the byproducts off the oxidation. Fractional distillation is advantageously carried out in a desorption column at overhead pressures of from 10 to 100 mm of Hg and temperatures of from 140° to 210° C. The move volatile impurities, such as benzoic acid and maleic anhydride, and volatile decomposition products of the solvent are taken overhead, whilst the phthalic anhydride is removed as a side stream. The solvent residues obtained as bottoms are returned to the wash column. This circulation of the solvent ensures that the amount of phthalic anhydride recovered in the desorption column is the same as that dissolved in the wash column.

The phthalic anhydride thus obtained may then, if desired, be subjected to conventional distillation for the purpose of producing a product of high purity.

The consumption of solvent is relatively low. It is approximately 15 kg per ton of phthalic anhydride recovered. Low-volatility by-products remaining in the solvent during the process may be readily removed therefrom by continuous decantation.

In another embodiment of the invention, the process gas is caused to flow countercurrently to the solvent in an adsorption column at temperatures of from 90° to 140° C and then in a quenching tower at temperatures of from 60° to 90° C. This causes the phthalic anhydride contained in the process gas to be dissolved by the solvent in the absorption column to an extent of from 50 to 80% and in the quenching tower to an extent of from 20 to 50%. It is advantageous to pass only a portion of the circulated solvent, i.e. about 15 to 40% thereof, through the quenching tower. This portion is then passed through a centrifuge or filtering equipment for mechanical preseparation of the solid portions of phthalic anhydride.

Finally, it is also possible to effect treatment of the process gases with the solvent only in a quenching tower at temperatures of from preferably 60° to 80° C.

The process of the invention produces phthalic anhydride from process gases in a particularly advantageous manner with simultaneous separation of byproducts of high and low volatilities.

Figure 2:
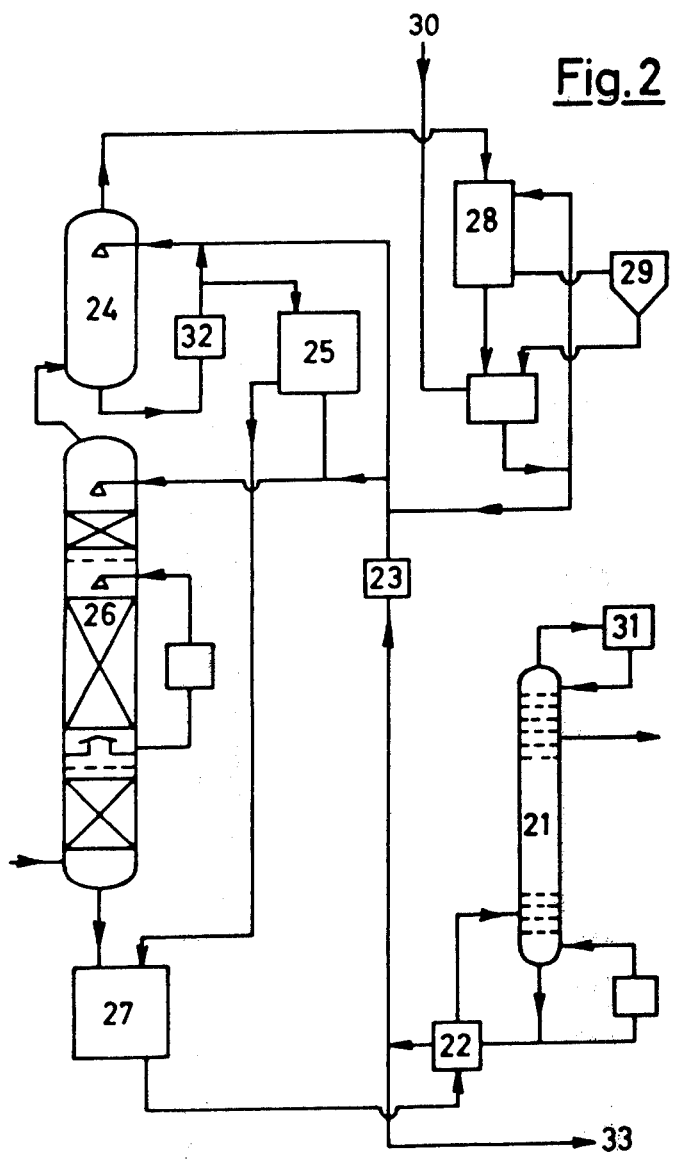

FIGS. 1 and 2 of the drawings are schematic representations of the units employed to recover phthalic anhydride in Examples 1 and 2, respectively.

EXAMPLE 1

Phthalic anhydride is recovered, in the manner illustrated in the accompanying FIG. 1, from a process gas produced by the atmospheric oxidation of o-xylene in contact with a fixed-bed catalyst, for example by the method described in German Published Application 1,643,703. The process gas, which has a temperature of 170° C and a phthalic anhydride content of 38 g/m$^3$ (STP), flows upwardly through an absorption column 3. The solvent, which consists of 64% by weight of $C_{26-36}$ paraffins, 32% by weight of naphthenes and 4% by weight of aromatics and which has a boiling point of 385° C/760 mm (determined by the method of German Standard DIN 51,356) and a residual content of phthalic anhydride of 0.2% by weight, leaves the centrifuge or filter 1 at a temperature of 40° C. It is then pumped to the top of the column 3 via a spiral heat exchanger 2. The solvent, which has a temperature of 70° C on entering the column 3, then flows down the column countercurrently to the process gas. Cooling stages installed in the column remove from the liquid mixture a portion of the heat of absorption and of the sensible heat of the process gases. The cooling stage 12 is set at 115° C and the cooling stage 13 at 85° C. The phthalic anhydride-laden solvent (Phthalic anhydride content about 3.5% by weight) is withdrawn from the bottom of the column at a temperature of 135° C and part of its passes through a spiral heat exchanger 4 for cooling in the bottom section of the absorption column and the remainder passes through the spiral heat exchanger 2 and a further spiral heat exchanger 5, in which a coolant is used, for cooling to 40° C before entering the centrifuge or filter 1. The slurry of phthalic anhydride crystals and solvent leaves the filter 1 to pass to a melting tank 6 heated, for example, with steam. The melt is passed through the spiral heat exchanger 4 and is looped back to the melting tank 6.

The spiral heat exchanger 4 of the bottom cooling stage of the absorption column also serves to withdraw part of the sensible heat of the process gas and the heat of absorption for the purpose of melting the phthalic crystals and for the thermal separation of the phthalic anhydride from the solvent in the desorption column 8.

A portion of the melt passes through spiral heat exchanger 7 to desorption column 8. The solvent is pumped from the bottom of the desorption column, after it has given off its heat to the feed in spiral heat exchanger 7, to the bottom of absorption column 3. The desorption column is operated at a pressure of 35 mm, the temperature at the bottom being 205° and that at the top being 150° C. The more volatile components of the process gas, whih have been absorbed by the solvent, and the more volatile decomposition products of the solvent are condensed in condenser 10 at the top of the desorption column. The phthalic anhydride is removed as a liquid side stream 14 and passed to a conventional phthalic anhydride distillation column for the production of a highly pure product. This column operates at a pressure of 20 mm and its temperature at the top is 150° C. The pure phthalic anhydride is removed as a gas therefrom at a point between its point of entry and the bottom of said column.

The process gas freed from phthalic anhydride leaves the top of the column as off-gas having a temperature of 75° C. Its final purity is 0.03% by weight of $SO_2$, 0.004% by weight of maleic anhydride, 0.001% by weight of benzoic acid and 0.001% by weight of phthalic anhydride.

When solvent has to be removed after long on-stream periods, this is done via line 15, whilst fresh solvent is fed to column 3 via line 16.

EXAMPLE 2

The process gas described in Example 1 passes up through an absorption column 26 and a quenching tower 24 in the manner illustrated in FIG. 2. Solvent having the composition specified in Example 1 and having a phthalic anhydride content of 5% by weight leaves the bottom of the desorption column 21 at a temperature of 200° C and passes through a spiral heat exchanger 22 for the transfer of heat to the phthalic anhydride-laden solvent stream fed to column 21. The solvent leaving said heat exchanger 22 passes through a further spiral heat exchanger 23 which is cooled by water or oil and in which the solvent is cooled to 60° C, whereupon 20% of said solvent passes to the top of the quenching tower 24 and 80% thereof to the top of column 26.

The solvent flows countercurrently to the process gas in the quenching tower, which gas has a temperature of from 95° to 110° C. In this way the residue of phthalic anhydride in the process gas (from 10 to 30% of the amount originally present in the process gas) is absorbed by the solvent.

In order to maintain the temperature of the solvent in the quenching tower 24 in the range 60° to 65° C, a portion of the solvent is circulated through a spiral heat exchanger 32 cooled with oil or water. The phthalic anhydride-laden solvent having a phthalic anhydride content of from 20 to 25% by weight passes to a centrifuge or filter unit 25 for separation of the phthalic anhydride crystals. The solvent substantially freed from solid phthalic anhydride passes, together with the major portion of solvent from the desorption column 21, to the absorption column 26 at a temperature of 60° C, in which column the major part of the exchange of material and heat takes place due to absorption occurring countercurrently to the process gas.

The phthalic anhydride-laden solvent leaves the bottom of column 26 at a temperature of 120° C and has a phthalic anhydride content of 7% by weight. It passes, together with the phthalic anhydride slurry leaving the centrifuge 25 and having a phthalic anhydride content of about 60% by weight, to a heated melting tank 27 and thence via a spiral heat exchanger 22 to the desorption column 21. The phthalic anhydride is separated by distillation in column 21 in the manner described in Example 1.

The treated process gas leaving the quenching tower 24 is advantageously passed through a Venturi washer 28 and a demister 29 in order to restrict off-gas Gosses via the solvent. Fresh solvent is continuously fed in through line 30. Solvent to be replaced is removed through line 33.

We claim:

1. A process for the continous recovery of phthalic anhydride from process gases obtained in the catalytic atmospheric oxidation of o-xylene or naphthalene which comprises: washing said process gases in an absorption column at a temperature of 60° to 170° C with a solvent consisting essentially of C26–44 paraffins or with a hydrocarbon mixture having a boiling point of at least 360° C at atmospheric pressure and containing at least 55% by weight of C26–44 paraffins, whereby phthalic anhydride from said process gases is dissolved in said paraffins; cooling said paraffins ladened with phthalic anhydride to form solid phthalic anhydride, separating said solid phthalic anhydride from the major portion of the solvent by mechanical means to form a slurry of phthalic anhydride crystals, melting said crystals and distilling said phthalic anhydride from said slurry; and recycling said paraffins to said absorption column.

2. A process as claimed in 1, wherein washing of the process gases with said solvent is carried out in a column at a temperature of from 70° to 140° C.

3. A process as claimed in claim 1, wherein the washing of the process gases with said solvent is carried out at temperatures of from 60° to 80° C in a quenching tower.

4. A process as claimed in claim 1, wherein the washing of the process gas with said solvent is carried out in a column at temperatures of from 90° to 140° C and then in a quenching tower at temperatures of from 60° to 90° C.

5. A process as claimed in claim 1 wherein said solvent consists essentially of C26–38 paraffins.

6. A process as claimed in claim 1 wherein said solvent leaves the absorption column at a temperature of 90°–135° C laden with from 0.5 to 40% by weight of phthalic and hydride.

* * * * *